US00PP16961P2

(12) United States Plant Patent
Olesen

(10) Patent No.: US PP16,961 P2
(45) Date of Patent: Aug. 8, 2006

(54) FLORIBUNDA ROSE PLANT NAMED 'POULCAS024'

(50) Latin Name: ***Rosa* hybrid**
Varietal Denomination: Poulcas024

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 11/131,739

(22) Filed: May 17, 2005

(51) Int. Cl.
*A01H 5/00* (2006.01)

(52) U.S. Cl. ..... Plt./148
(58) Field of Classification Search ..... Plt./148, Plt./141, 150
See application file for complete search history.

*Primary Examiner*—Kent Bell
*Assistant Examiner*—June Hwu

(57) ABSTRACT

A new garden rose plant of the floribunda class which has abundant, pink blend flowers and attractive foliage. This new and distinct variety has shown to be uniform and stable in the resulting generations from asexual propagation.

3 Drawing Sheets

Botanical designation: *Rosa* hybrid.
Variety denomination: 'Poulcas024'.

SUMMARY OF THE INVENTION

The present invention constitutes a new and distinct variety of garden rose plant which originated from a controlled crossing between the female seed parent, an unnamed seedling, and the male pollen parent 'Poulcs007', a variety created by the same inventor described and illustrated in U.S. Plant Pat. No. 15,161.

The two parents were crossed during the summer of 1995 and the resulting seeds were planted in a controlled environment in Fredensborg, Denmark. The new variety, named 'Poulcas024', originated as a single seedling from the stated cross.

The new variety may be distinguished from its female seed parent by the following combination of characteristics:

1. The seed parent has 40 to 45 petals. 'Poulcas024' has 300 to 315 petals.
2. Flowers of the seed parent have a general tonality of Red Group 47C, while flowers of 'Poulcas024' are Red Group 49A to 49B with intonations of Red Group 52C.

The new variety may be distinguished from its male pollen parent by the following combination of characteristics:

1. The pollen parent has 75 to 80 petals. 'Poulcas024' has 300 to 315 petals.
2. Flowers of the pollen parent have a general tonality of Red Group 49B, while flowers of 'Poulcas024' are Red Group 49A to 49B with intonations of Red Group 52C.

The objective of the hybridization of this rose variety was to create a new and distinct variety for garden use with unique qualities, such as:

1. Uniform and abundant pink blend flowers;
2. Vigorous, but compact growth when propagated both as a budded rose and on its own roots;
3. Exceptional disease resistance.

This combination of qualities is not present in previously available commercial cultivars of this type, known to the inventors, and distinguish 'Poulcas024' from all other varieties of which we are aware.

As part of the rose development program, Mogens N. Olesen germinated the seeds from the aforementioned hybridization during winter of 1995 and conducted evaluations on the resulting seedlings in a controlled environment in Fredensborg, Denmark. 'Poulcas024' was selected in the spring of 1996 by the inventor as a single plant from the progeny of the aforementioned hybridization.

Asexual reproduction of 'Poulcas024' by traditional budding and rooted cuttings was first done by Mogens N. Olesen in the nursery in Fredensborg, Denmark in July, 1996. This initial and other subsequent asexual propagation conducted in controlled environments have demonstrated that the characteristics of 'Poulcas024' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulcas024'. Specifically illustrated in the drawing are:

FIG. 1.1; Cluster of flower buds partially opened showing attachment of leaves and pedicels;

FIG. 1.2; Open flower;

FIG. 1.3; Sepals, receptacle, and peduncle;

FIG. 1.4; Flower petals, detached;

FIG. 2.1; Mature leaves;

FIG. 2.2; Bare stems exhibiting thorns;

FIG. 3.1 Juvenile leaf, underside;

FIG. 3.2 Juvenile leaf, upper side;

FIG. 3.3 Juvenile stem and leaves.

DETAILED DESCRIPTION OF THE VARIETY

The following is a description of 'Poulcas024', as observed in its growth in a field nursery in Jackson County, Oreg. Observed plants are 3 years of age, and were grown on *Rosa multiflora* understock. Color references are made using The Royal Horticultural Society (London, England) Colour Chart, 2001, except where common terms of color are used.

For a comparison, several physical characteristics of the rose variety 'Pouldron', described and illustrated in U.S. Plant Pat. No. 10,923 dated May 25, 1999 are compared to 'Poulcas024' in Chart 1.

CHART 1

| | 'Poulcas024' | 'Pouldron' |
|---|---|---|
| Petal Count | 300–315 | 44 to 58 |
| Flower Diameter | 40 mm | 70–85 mm |
| General Tonality of Flower Color | 49A to 49B with intonations of 52C | 49B to 39D |

FLOWER AND FLOWER BUD

Blooming habit: Continuous.

Flower bud:

*Size.*—Upon opening, 22 mm in length from base of receptacle to end of bud. Bud diameter is 14 mm.

*Bud form.*—Urceolate with pointed apex.

*Bud color.*—As sepals begin to unfold, petals are Greyed-Red Group 180B to Red Group 39B with intonations of Red Group 46A. As sepals further unfold, petals are Greyed-Red 179C with intonations of Greyed-Red Group 180C and Red Group 48A.

*Sepal inner surface.*—Color: Green Group 138B. Anthocyanic pigments Greyed-Purple Group 183B to Greyed-Purple Group 184A. Surface: Weak pubescence observed.

*Sepal outer surface.*—Color: Yellow-Green Group 144A. Texture: Somewhat rough with many stipitate glands.

*Sepal shape.*—Apex: Cirrhose. Base: Flat at union with receptacle.

*Sepal margin.*—Margins have weak foliaceous appendages on three of the five sepals.

*Sepal size.*—Normally 25 mm long by 6 mm wide.

*Receptacle.*—Texture: Smooth pubescent. Stipitate glands observed in light quantity. Shape: Funnel shaped. Size: 9 mm (h)×9 mm (w). Color: Yellow-Green Group 144A.

*Peduncle.*—Color: Yellow-Green Group 144B. Surface: Smooth with thorns. Length: 3 to 4 cm. Diameter: 4 mm.

*Pedicel.*—Surface: Very rough with stipitate glands. Length: 40 to 45 mm on average. Diameter: 2.5 mm on average. Color: Yellow-Green Group 144B. Anthocyanic pigments the color of Orange Group 175A observed. Strength: Strong. Scent: Stipitate glands release a strong fruity scent.

Flower bud development: Flower buds are borne singularly and in clusters of 5 buds per flowering stem. Inflorescence type: Panicle.

Flower bloom:

*Fragrance.*—Medium rose scent.

*Duration.*—The blooms have a duration on the plant of approximately 14 to 21 days. Petals do not fall cleanly away from plant after flowers have fully matured.

*Size.*—Flower diameter is 40 mm when open. Flower depth is 26 mm.

*Flower shape.*—General shape is a globular until flowers are fully mature. Afterward, flowers resemble a rosette with many overlapping petals, packed into numerous sections.

*Shape of flower, side view.*—Upon opening the upper portion is convex. The lower portion is flat. After opening, the upper portion is convex. The lower portion is concave.

Petalage: Under normal conditions, flowers have 300 to 315 petals total, 45 of which are petaloids.

Petal color:

*Upon opening, outermost petals.*—Upper surface: Greyed-Orange Group N170B with intonations of Orange-Red Group 35B. Light intonations of Yellow-Green Group 145B throughout the petal. Lower surface: Red Group 49A to Greyed-Red Group 182B and 182C with intonations of Yellow-Green Group 145B.

*Upon opening, inner petals.*—Upper surface: Red Group 43D to 41D with intonations of Orange-Red Group 32D toward petal base. Lower surface: Red Group 49A to 49B with intonations of Red Group 49D.

*Basal petal spots, upon opening.*—Upper surface: Yellow-Green Group 145C to 145D. Lower surface: Yellow-Green Group 145D.

*After opening, outer petals.*—Upper surface: Red Group 49A. Lower surface: Red Group 55B to 54C with streaking and light intonations the color of Red Group 49B.

*After opening, inner petals.*—Upper surface: Red Group 38B to 36B with light intonations of Orange Group 29B. Lower surface: Red Group 39C to 39D to Red Group 49B.

*Basal petal spots, after opening.*—Upper surface: Yellow Group 4B. Lower surface: Yellow Group 4C.

General tonality: On open flower Red Group 49A to 49B with intonations of Red Group 52C.

Petals:

*Petal reflex.*—Flat.

*Margin.*—Entire with occasional point at the center of the margin. Weak undulations of margin observed.

*Shape.*—Generally narrow elliptical. Apex shape: Rounded. Base shape: Acute.

*Size.*—Outer petals: 30 mm (l)×25 mm (w). Inner petals: 17 mm (l)×11 mm (w). Petal size progressively decreases toward the flower center.

*Texture.*—Smooth.

*Thickness.*—Average.

*Arrangement.*—Not Formal.

Petaloids:

*Quantity.*—45 on average.

*Size.*—10 mm (l)×6 mm (w).

*Shape.*—Narrow elliptical with acute apex. Petaloids are sometimes irregular with highly undulated margins.

*Color.*—Upper: Red Group 38B to 36B. Lower: Red Group 39C to 39D to 49B.

*Color variation.*—Some petaloids have distinct coloration with an upper surface the color of Red Group 34A. Lower surface is Red Group 40A to 41B.

Reproductive organs:

*Pollen.*—None observed.

*Anthers.*—Size: 2 mm in length. Color: Yellow-Orange Group 18A to B. Quantity: Normally 30.

*Filaments.*—Color: Yellow Group 1A. Length: 5 mm.

*Pistils.*—Length: 12 mm. Quantity: 75 to 80.

*Stigmas.*—Very superior in location relative to the length of the filaments and the height of the anthers. Color: Yellow-Green Group 145C to 145D.

*Styles*.—Color: Yellow-Green Group 145C to 145D.

*Hips*.—None Observed in the field nursery in Jackson County Oreg.

PLANT

Plant growth: Moderate, upright to bushy. When grown as a budded field grown plant on *Rosa multiflora* understock, the average height of the plant is 60 to 100 cm and the average width is 50 to 60 cm.

Stems:

*Color*.—Juvenile growth: Yellow-Green Group 146C. Mature growth: Yellow-Green Group 146B.

*Length*.—On average, canes are 23 cm from the base of the plant to the flowering portion.

*Diameter*.—5 mm.

*Internodes*.—On mature canes, there is an average distance of 22 mm between nodes.

*Surface texture*.—Young wood: Smooth. Older wood: Smooth.

Thorns:

*Incidence*.—11 thorns per 10 cm of stem.

*Size*.—Average length of thorns on mature stems is 4 to 5 mm.

*Shape*.—Upper side: Flat. Lower side: Concave.

*Color*.—Juvenile thorns: Greyed-Yellow Group 160B to Yellow-Green Group 145B. Mature thorns: Greyed-Yellow Group 160A with intonations of Yellow-Green Group 144C.

Plant foliage: Normal number of leaflets leaves in middle of stem: 7 leaflets.

*Compound leaf*.—90 to 105 mm in length by 60 to 70 mm wide.

*Quantity*.—4 leaves per 10 cm of stem on average.

*Color of mature foliage*.—Upper side: Yellow-Green Group 147A. Lower side: Yellow-Green Group 147B.

*Color of juvenile foliage*.—Upper side: Yellow-Green Group 144A. Lower side: Yellow-Green Group 144A. Anthocyanic intonations: Greyed-Orange Group 166A to 166B. Location: Generalized and at the margins.

Plant leaves and leaflets:

*Stipules*.—Size: 10 to 14 mm in length. Shape: Linear, slightly broad based with outward extending apecies. Margins: Finely serrated with stipitate glands. Color: Yellow-Green Group 146A.

*Petiole*.—Length: 15 mm. Diameter: 2 mm. Upper surface: Color: Yellow-Green Group 146A. Observations: Few stipitate glands on the upper margins. Lower surface: Color: Yellow-Green Group 146C. Observations: Small prickles.

*Rachis*.—Length: 50 mm on average. Upper surface: Color: Yellow-Green Group 146A. Observations: Few stipitate glands. Lower surface: Color: Yellow-Green Group 146C. Observations: Few small prickles.

*Leaflet*.—Edge: Doubly serrated. Size: Average size of the terminal leaflet on normal leaves is 40 to 45 in length by 25 to 28 mm wide. Shape: Generally elliptical. Base: Acuminate. Apex: Acuminate to mucronate.

*Texture*.—Smooth. Thickness: Average. Arrangement: Odd pinnate. Venation: Reticulate. Glossiness: Moderate glossy.

Disease resistance: Above average resistance to downy and powdery mildew, rust, black spot, and *Botrytis* under normal growing conditions in Jackson County, Oreg.

Cold hardiness: The variety is tolerant to USDA Cold Hardiness Zone 6.

Heat tolerance: The variety has been found to be suitable for climate conditions found in the American Horticulture Society heat zone 7.

It is claimed:

1. A new and distinct variety of rose plant of the floribunda rose class named 'Poulcas024', illustrated and described herein, due to its abundant pink blend flowers, disease resistance, and extended period of bloom.

* * * * *

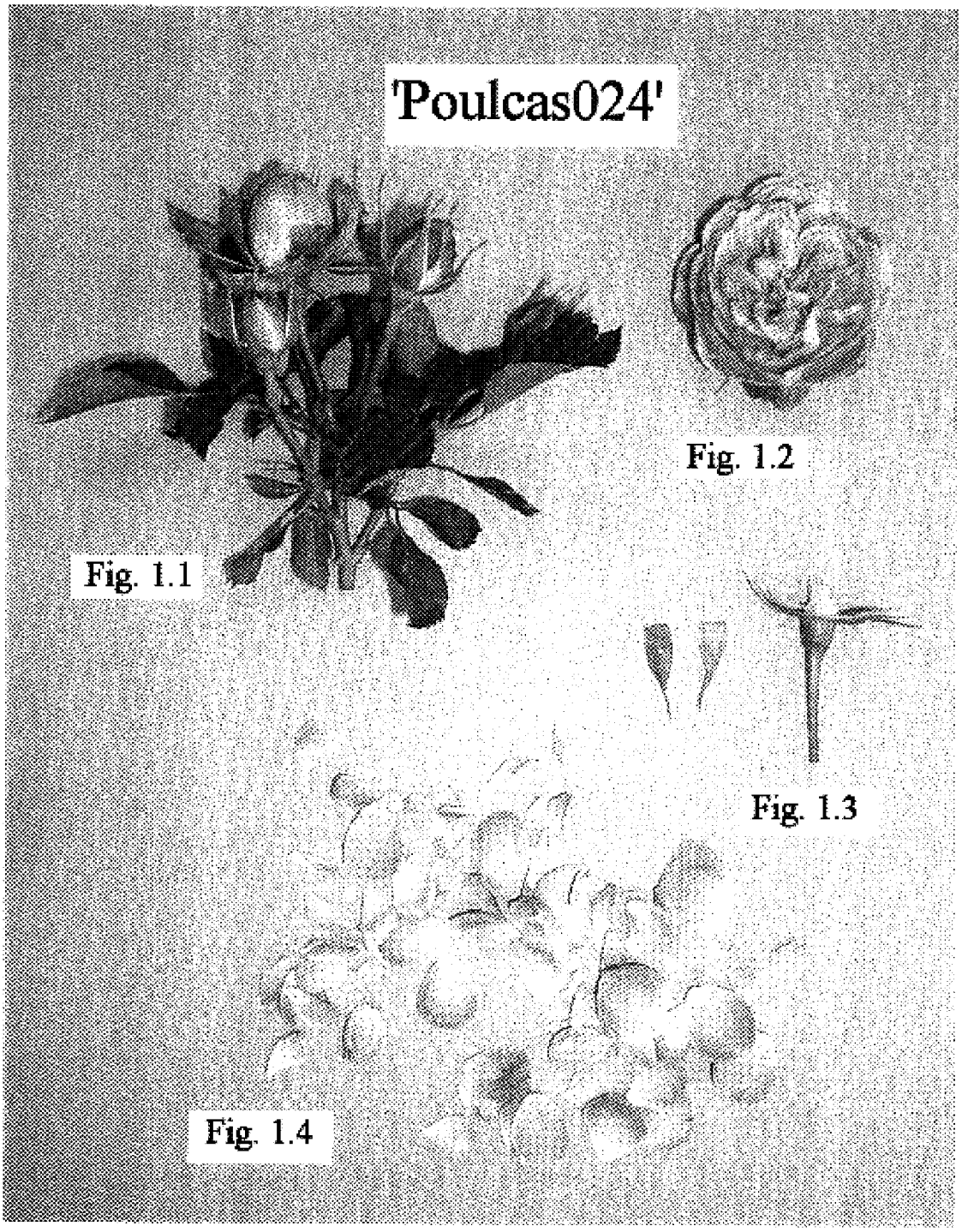
'Poulcas024'
Fig. 1.1
Fig. 1.2
Fig. 1.3
Fig. 1.4

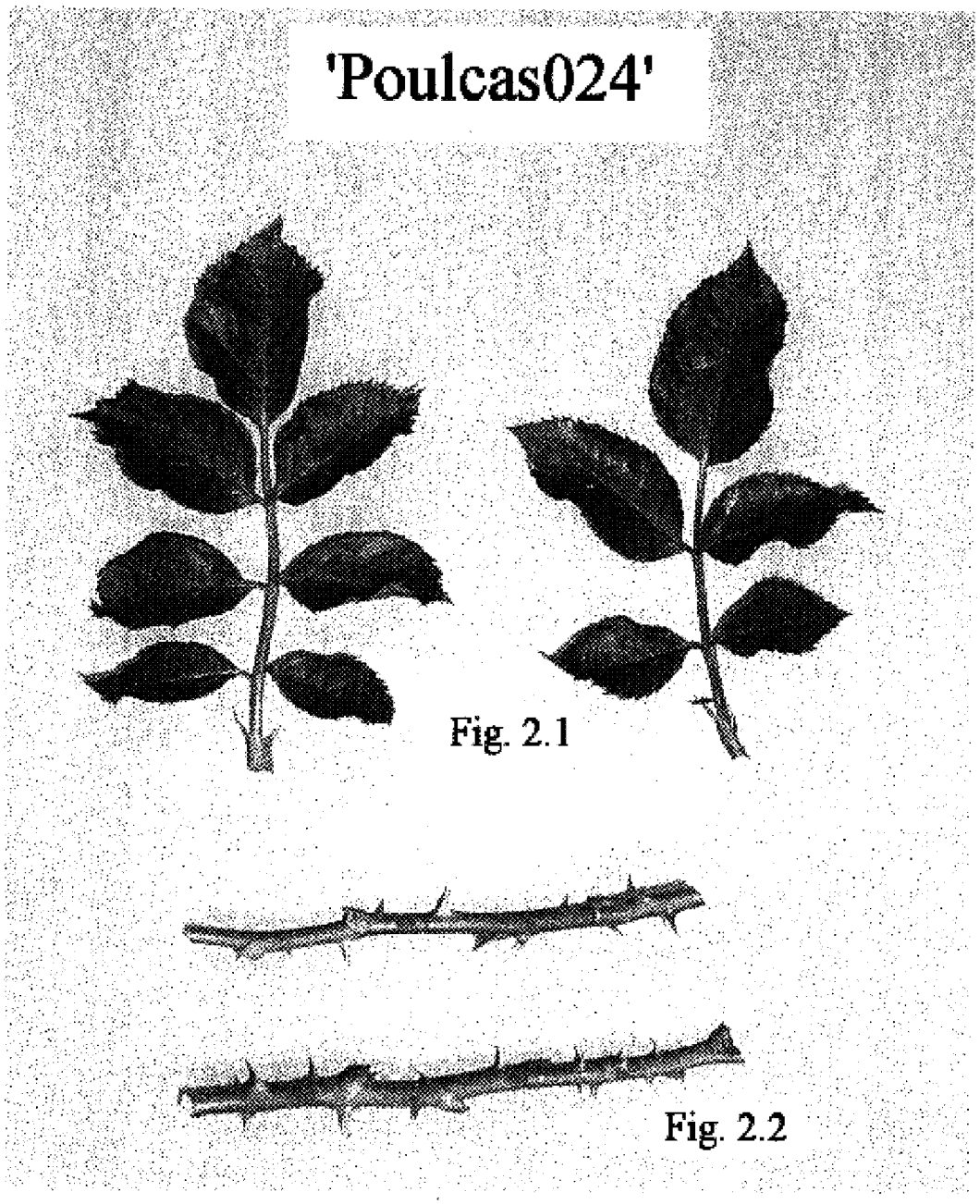
'Poulcas024'
Fig. 2.1
Fig. 2.2

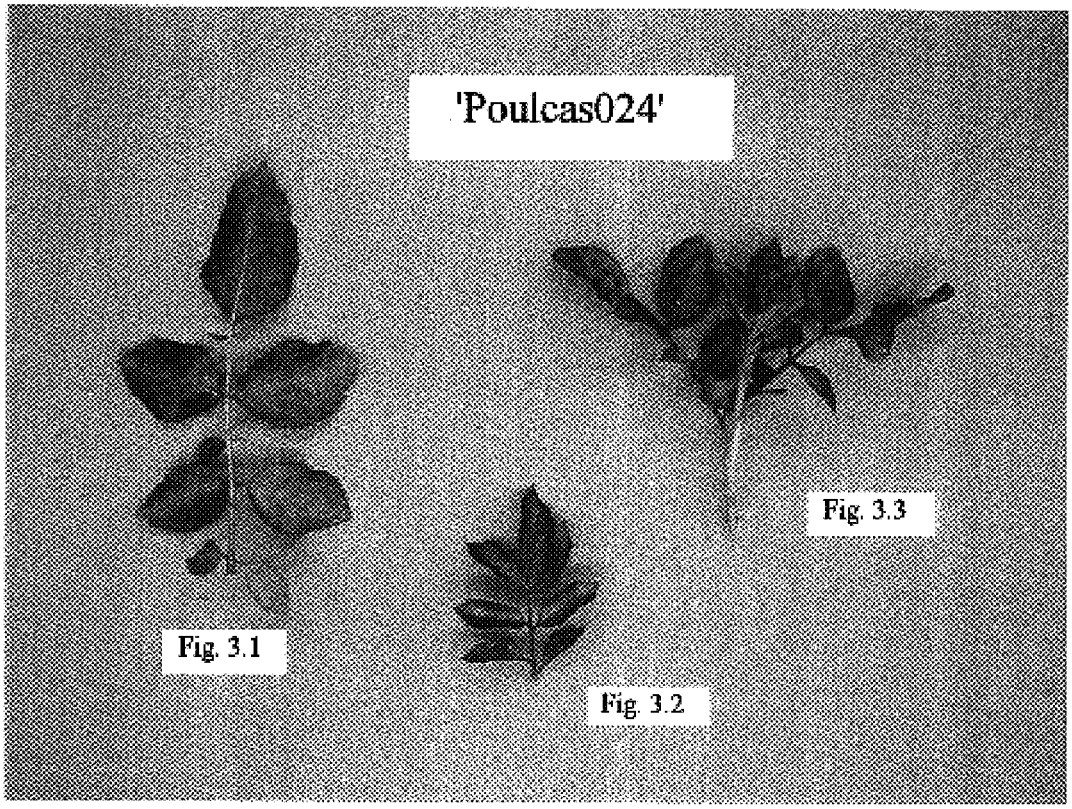
'Poulcas024'
Fig. 3.1
Fig. 3.2
Fig. 3.3